Figure 1:
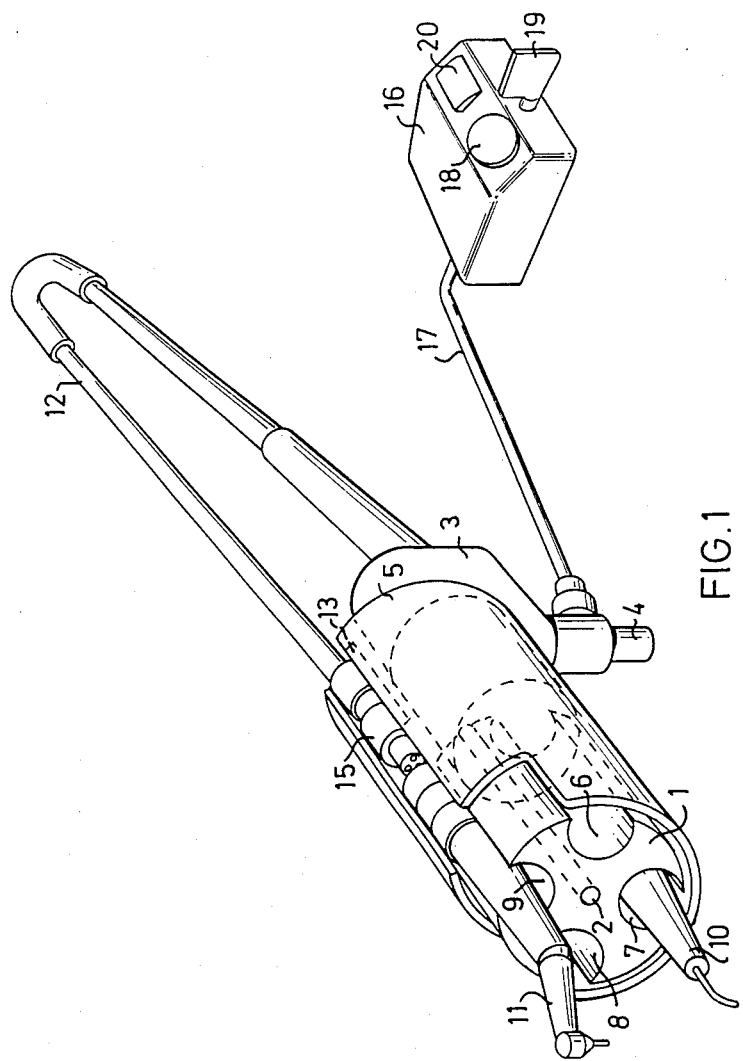

United States Patent [19]

Timerdahl et al.

[11] Patent Number: 4,648,839
[45] Date of Patent: Mar. 10, 1987

[54] CARRIER DEVICE FOR HAND TOOLS, FOR USE IN DENTAL WORK

[75] Inventors: Ake Timerdahl, Värmdö ; Jan Angseryd, Trangsund, both of Sweden

[73] Assignee: Landstingens Inkopscentral, Lic, Ekonomisk Forenting, Solna, Sweden

[21] Appl. No.: 768,336

[22] Filed: Aug. 22, 1985

[30] Foreign Application Priority Data

Aug. 31, 1984 [SE] Sweden .................................. 8404369

[51] Int. Cl.⁴ .................................. A61C 1/14
[52] U.S. Cl. ..................................... 433/77
[58] Field of Search .............................. 433/77, 78, 79

[56] References Cited

U.S. PATENT DOCUMENTS 1,972,072 9/1934 Angell ..................................... 433/78

Primary Examiner—Robert Peshock
Attorney, Agent, or Firm—Young & Thompson

[57] ABSTRACT

The invention relates to a carrier device for hand tools for use in dental work. The carrier device incorporates holders for the tools and a supply for supplying pressurized air, water and/or electrical power to the tools. In accordance with the invention a magazine is arranged to carry the tools, and is movable in a manner to enable a selected tool to be moved to a pick-up station. The supply according to the invention comprises a single, flexible supply conduit incorporating channels for pressurized air, water and/or electrical power, and the tools and the supply conduit are provided with couplings for connecting a selected tool to the supply conduit in the pick-up station.

3 Claims, 2 Drawing Figures

CARRIER DEVICE FOR HAND TOOLS, FOR USE IN DENTAL WORK

The invention relates to a carrier device for hand tools, preferably for use in dental work, the device including tool holders and supply means for supplying pressurized air, water and/or electrical power to the tools.

In previously known carrier devices for hand tools used by dentists, there has been used one holder for each individual tool or instrument together with separate supply means for the supply of pressurized air, water and/or electrical power to the tools. Since each tool must be movable within a relatively wide working range and since a conventional instrument or tool kit incorporates a plurality of instruments or tools, there results a large number of supply means, in the form of pipes and the like, which are expensive and space-consuming and give rise to problems relating to hygiene. In addition separate control means are required for the various instruments or tools, which further adds to the costs and to the risk of malfunctioning of the apparatus.

The object of the present invention is to provide a carrier device of the kind disclosed in the introduction with which the aforesaid disadvantages are eliminated, which is of simple construction, and which affords a greater degree of flexibility with respect to the instruments or tools used. This object is mainly achieved in accordance with the invention by providing the carrier device with a tool-carrying magazine which is movable in a manner to enable a selected tool to be advanced to a pick-up station; by constructing the supply means in the form of a single, flexible supply conduit incorporating channels for pressurized air, water and/or electrical power; and by providing the tools and the supply conduit with coupling means for connecting a selected tool to the supply conduit in the pick-up station.

Figure 2:
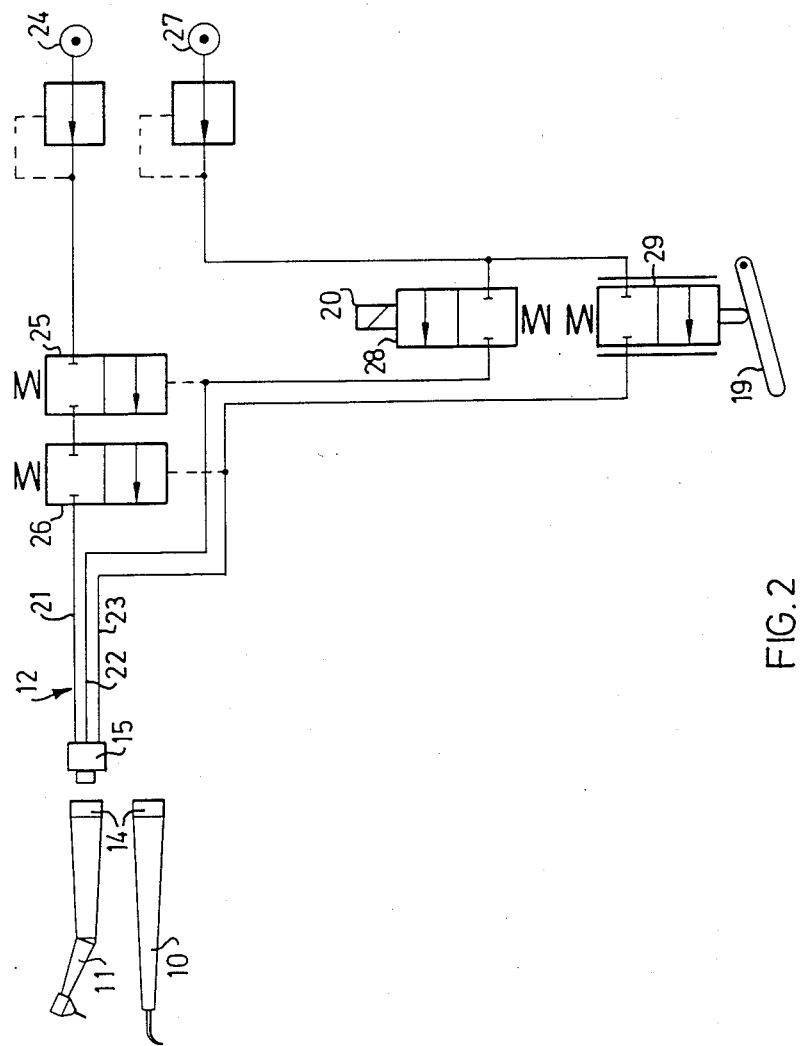

The invention will now be described in more detail with reference to the accompanying drawings, in which FIG. 1 is a schematic view, substantially in perspective, of one embodiment of a carrier device according to the invention, and FIG. 2 is a coupling diagram illustrating the supply of water and pressurized air to the device illustrated in FIG. 1.

The carrier device illustrated in FIG. 1 includes a substantially cylindrical drum 1 which can be rotated about an axis 2 with the aid of a drive means 3, which also supports the drum 1. The drive means 3 is supported in turn by an attachment means 4, which is intended to be mounted for rotation in a holder (not shown). Located around the drum 1 is a casing 5, the configuration and function of which will be described more fully hereinafter.

The drum 1 forms a magazine for a plurality of hand tools or instruments and is provided with a number of tool or instrument accommodating recesses 6-9. Although the illustrated drum has four recesses 6-9, it will be understood that a greater or lesser number of recesses may be provided, depending on the number of tools or instruments involved. Only two tools are shown in FIG. 1, namely a tool 10 accommodated in the recess 7 and a tool 11 in the recess 9.

Each of the recesses 6-9 is substantially semicylindrical in shape and is open towards the periphery of the drum 1. When the drum 1 occupies the position shown in FIG. 1, the tool 11 in the recess 9 is located in a pick-up station in which the casing 5 surrounding the drum 1 is provided with a groove which permits the tool 11 to be removed from the recess 9 radially in relation to the drum 1.

In order to enable the tool or instrument to be used, it is necessary to supply pressurized air, water and/or electrical power thereto, this being achieved through a flexible supply conduit 12 which is connected at one end thereof to the drive means 3 or to the attachment means 4, and at the other end is removably insertable into a holder means 13 attached to the casing 5 at a location adjacent the groove therein.

The inner or rearward end of each instrument or tool 10,11 is provided with a coupling means 14 which is intended to co-act with a coupling means 15 located on that end of the supply conduit 12 which co-acts with the holder means 13. The coupling means 14 and 15 are designed to enable a respective tool 10,11 to be coupled to the supply conduit 12 when said tool is located in the pick-up station, the coupling means 14 and 15 being connected together by pushing one coupling means axially into the other. This coupling movement of the coupling means is suitably effected by causing the rotatable drum 1 to effect a forward and backward movement in the axial direction with the aid of the drive means 3, this movement being utilized to couple together and to separate the coupling means 14 and 15. Subsequent to connecting the coupling means 14 and 15 together, the tool 11 can be removed from the recess 9, and the end of the supply conduit 12 from the holder means 13. When work with the tool 11 has been completed, the tool is replaced in the recess 9 and the coupling means 14 and 15 disconnected, by pulling the same axially apart. The drum 1 can then be rotated to position another tool in the pick-up station, whereupon this tool can be connected to the supply conduit 12 through the agency of the coupling means 14 provided on said tool.

As will be seen from FIG. 1, the instruments or tools 10,11 can be remotely controlled through an operating assembly 16, which is connected to the supply conduit 12, via the attachment means 4, by means of a line 17. The operating assembly 16 is provided in turn with supply lines for pressurized air, water and/or electrical power (not shown). The operating assembly 16 is provided with an operating means 18 intended for actuation of the drive means 30 for rotation of the drum 1 about the axis 2 for changing tools. The operating assembly 16 is also provided with a control means 19 for operating the tool which is at that time connected to the supply conduit 12. The operating assembly 16 is also provided with operating means 20 for controlling the supply of water to the tool in question. The construction of the operating assembly 16 is described in more detail hereinafter.

FIG. 2 is a coupling diagram illustrating the construction of the operating assembly 16 with regard to the supply of water and pressurized air to the tools or instruments 10,11. As will be seen from FIG. 2, the supply conduit incorporates a water-supply line 21 and two pressurized-air lines 22 and 23 respectively. Water is supplied to the line 21 from an inlet line 24, via two sequentially arranged valves 25 and 26 respectively, while pressurized air is supplied to the line 22 from an inlet line 27 via a valve 28 which is actuated by the operating means 20, and pressurized air is supplied to the line 23 from the inlet line 27 through a valve 29 controlled by the operating means 19.

When using the supply conduit 12 constructed in accordance with the FIG. 2 embodiment, the line 21 is used to supply flushing and cooling water to the relevant tool, while the line 22 is used to convey pressurized air to the tool for clean-blowing purposes and the line 23 is used to supply pressurized air for driving a pressurized-air motor located in the tool in question. The functions of the various elements will be evident from FIG. 2, therewith rendering any further description of these functions unnecessary.

In addition to the elements shown in FIG. 2, the line 17 also includes control lines for the drive means 3 for rotating the drum 1 and for connecting and disconnecting the coupling means 14 and 15. These functions can be carried out either electrically, pneumatically or hydraulically.

It will be understood that the invention is not restricted to the aforedescribed embodiment, and that modifications can be made within the scope of the following claims.

We claim:

1. A carrier device for selecting different hand tools for use in dental work, comprising holders for different tools, and supply means for supplying pressurized air and water to the tools, a magazine to carry the tools movable in a manner to enable a selected tool to be moved to a pick-up station; the supply means located at said pick-up station comprising a single, flexible supply conduit incorporating channels for pressurized air and water; and the tools and the supply conduit having respective coupling means for connecting a selected tool to the supply conduit in the pick-up station.

2. A carrier device according to claim 1, in which the magazine includes a rotatable drum having a recess for each tool, said recesses being open in a radial direction, the drum being located in a casing which closely embraces the drum along the major part of its periphery and is provided with an opening at the pick-up station for enabling removal of the tool located in the pick-up station in a radial direction.

3. A carrier device according to claim 1, in which the coupling means on the tools and the supply conduit are arranged to effect interconnection when the two coupling means are pressed axially together;, and the drum is reciprocally movable in an axial direction in a manner to connect and disconnect the supply conduit to and from the tool located in the pick-up station.

* * * * *